United States Patent [19]

Morgan

[11] Patent Number: 5,128,259
[45] Date of Patent: Jul. 7, 1992

[54] FACTOR-DEPENDENT HEMATOPOIETIC CELL LINE EXHIBITING EPO-INDUCED ERYTHROCYTE MATURATION

[75] Inventor: Doris A. Morgan, Voorhees, N.J.

[73] Assignee: Hahnemann University, Philadelphia, Pa.

[21] Appl. No.: 428,173

[22] Filed: Oct. 27, 1989

[51] Int. Cl.$^5$ .............. C12N 5/00; C12N 5/02; C12N 1/00

[52] U.S. Cl. .................. 435/240.2; 435/240.1; 435/240.25; 435/948

[58] Field of Search ............. 435/240.1, 240.2, 240.25, 435/948

[56] References Cited

PUBLICATIONS

Morgan et al., "Novel peripheral blood-derived human cell lines with properties of megakaryocytes", The Journal of Cell Biol., vol. 100, 565-573, 1985.

*Primary Examiner*—John Doll
*Assistant Examiner*—Gail Poulos
*Attorney, Agent, or Firm*—Dann, Dorfman, Herrell and Skillman

[57] ABSTRACT

Factor-dependent cell line, HU-01, provides the first in vitro system in which human CD34 positive hematopoietic cells have been induced to undergo complete differentiation into enucleated hemoglobin-containing erythrocytes. HU-01 cells may provide a source of monoclonal antibodies useful for early diagnosis and possible treatment of human leukemia conditions, as well as of regulatory factors having therapeutic utility.

3 Claims, 4 Drawing Sheets

FACTOR-DEPENDENT HEMATOPOIETIC CELL LINE EXHIBITING EPO-INDUCED ERYTHROCYTE MATURATION

The U.S. Government has certain rights in the invention described herein, which was made in part with funds from the National Institutes of Health.

FIELD OF THE INVENTION

This invention relates to a unique factor-dependent cell line comprising hematopoietic progenitor cells which undergo erythropoietin-induced differentiation in vitro into enucleated hemoglobin-containing erythrocytes.

BACKGROUND OF THE INVENTION

Cell lines of hematopoietic cells have been useful tools in studying the growth and differentiation of immature blood cells. The promyelocytic cell line HL60, Collins, *Nature*, 298:629 (1982), and the erythroleukemia-derived cell lines HEL, Martin et al., *Science*, 216:1233 (1982). and K562, Loggin et al., *Blood*, 45:321 (1978), having phenotypes characterized by both platelet and erythrocyte properties, have been extensively studied, but are restricted in their capacity to differentiate in response to chemical and biological inducers. Other leukemia-derived cell lines which are dependent upon recombinant growth factors have recently been reported and represent several maturation stages of myeloid or lymphocytic lineages. Ihle, *International J. Cell Cloning*, 7:68 (1989).

Factor-dependent colonies of erythrocytes have been obtained from fresh human bone marrow (Perrine et al., *Biochem. Biophys. Res. Comm.*, 148:694 (1987)) and peripheral blood (Rovera et al., *Anal. Biochem.*, 85:506 (1987)) in semi-solid culture systems. Even though these biological systems have contributed significantly to the understanding of erythropoiesis, they too have been limited in their capacity to represent the complete differentiation pathway beginning with a noncommited progenitor and ending with a mature hemoglobin-containing erythrocyte.

Factor-dependent cell lines with properties of megakaryocytes have recently been reported. Avanzi et al., *Brit. J. Haem.*, 69:359 (1988). Most of the characterization of megakaryocytes, both past and present, has been achieved using either the transformed cell lines or megakaryocytes freshly isolated from bone marrow before and after short-term cultures in either suspension or in colony assays. The conventional techniques used to characterize these cells have been morphology in culture, surface and cytoplasmic phenotype, as determined by monoclonal and polyclonal antibodies, biochemical studies of the synthesis of lineage-specific proteins or ultrastructure by electron microscopy. However, a well-defined phenotype for megakaryocytes has not yet been established. The cell lines as well as the uncultured early leukemic blasts have a mixed phenotype in that both megakaryocyte and erythroid markers appear within the same population of cells. This may be attributed to several factors, including (i) lineage infidelity of leukemic cells due to aberrant differentiation, (ii) wider distribution of markers on other lineages, or presence of markers before occurrence of lineage commitment and (iii) cellular expression of markers of more than one lineage for a brief period of time during the process of differentiation, before loss of properties not associated with the more mature stages. One possibility arising from these alternatives is the existence of a common precursor for erythroid and megakaryocytic lineages. Dessypris et al., *Brit. J. Haem.*, 65:265 (1987). If such a cell exists, one must look for the earliest events associated with the event of lineage commitment, which would be at the level of gene expression. The standard methodology used for cell characterization reflects very late events subsequent to protein synthesis and does not provide crucial information regarding gene activation. Molecular techniques have not been widely used in the study of hematopoiesis due to either the limited numbers of cultured fresh cells, or the differentiation restriction of the transformed cell lines. One exception is the study of the globin gene switch in the committed erythroid cell.

Molecular and cellular biological methods have been used to characterize the globin genes and the natural course of the globin gene switch in which fetal gamma globin is replaced by adult beta globin. This gene switch occurs in development during the first year of life and also during adult bone marrow hematopoiesis. Much information has been derived from studies on human cell lines induced to produce minute amounts of adult hemoglobin, as well as on the MEL murine virus-induced erythroleukemia cell line, but globin gene modulation in these systems occurs in a renewing population of cells. T. Rutherford et al., *Nature* 280, 164 (1979); P. Martin et al., *Science*, 216, 1233 (1982); and M. Kaku et al., *Blood*, 64, 314 (1984). Although fresh erythroid cells have been grown in colony assays, the progeny of the progenitor cells are virtually inaccessible for the study of molecular events of gene expression. *Molecular Basis of Blood Diseases*: Hemoglobin Switching, p. 74, J. Dyson, ed., Saunders (1987).

There is a need for a biologically-relevant in vitro human system in which (i) cells can undergo a natural progression of erythroid maturation including the production of fetal and then adult hemoglobin; (ii) proliferation can be selectively and biologically inhibited before the induction of erythropoiesis and during the gene switch; and (iii) sufficient numbers of cells are readily available at select times during maturation for molecular analyses.

SUMMARY OF THE INVENTION

In accordance with the present invention, there is provided a cultured, factor-dependent hematopoietic human cell line, designated HU-01, which exhibits EPO-induced terminal erythrocyte maturation.

Insofar as is known, this factor-dependent cell line is the first in vitro system comprising the human biopotential progenitor of megakaryocytes or of erythrocytes, in which human CD-34 and glycophorin A (GPA) positive hemotopoietic cells, having no detectable lymphocyte markers, are inducible by erythropoietin (EPO) to erythroid commitment with complete differentiation into enucleated hemoglobin-containing erythrocytes.

BRIEF DESCRIPTION OF THE DRAWINGS

Referring to the drawings herein.

DESCRIPTION OF THE PREFERRED EMBODIMENT

The cell line of the invention was derived from a patient who had progressed from myelofibrosis and myeloid metaplasia to acute megakaryoblastic leukemia (M7), within two years. The circulating blood had a 10-fold increase in white blood cells and contained greater than 80% megakaryoblasts as defined by platelet-specific membrane glycoproteins (GP)Ib and GP IIb-IIIa and a distinctive pattern of cytoplasmic blebbing, as described by Bennett et al., *Annals Int. Med.*, 103:460 (1985). The cells had no detectable lymphocyte markers. The karyotype of the bone marrow was hypodiploid with a modal chromosome number of 44XY and all of the dividing cells belonged to an abnormal clone characterized by additions to the short arms of chromosomes 1 and 3, the loss of chromosomes 4, 5, 15 and 19 and the addition of two ring chromosomes.

Growth and differentiation of the primitive cells were assayed in a liquid culture system, which has been described elsewhere. See: Morgan et al., *Science*, 193:1007 (1976). The cultures were supplemented with rh growth factors known to have an effect on megakaryocytes, as reported by Briddell et al., *Blood*, 72:317a (1988); and Dessypris et al., supra.

Figure 1:
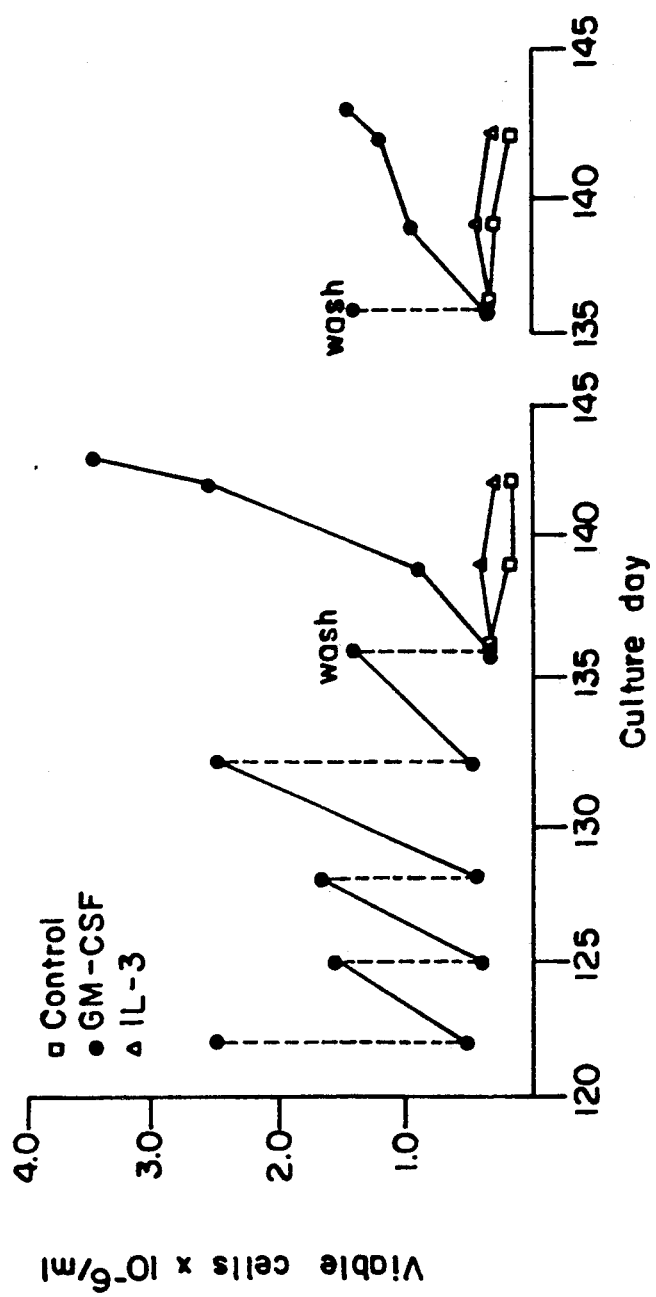
FIG. 1(A) and 1(B) are a graph representing the correlation between cell proliferation and length of time in culture for cultured HU-01 cells grown in the presence of recombinant human (rh) granulocyte macrophage colony-stimulating factor (GM-CSF) and rh interlukin-3 (IL-3) and illustrates the strict requirement of GM-CSF for continuous growth (the dashed vertical lines signify culture splitting to decreased cell density)

The early culture period showed a growth response that was not predicted. During the first 2 weeks of culture, exposure to IL-3 or GM-CSF enhanced proliferation of the primitive cells, as compared to a control culture, with some limited maturation to probable megakaryocytes. After the initial response to IL-3, cells showed a gradual growth decline and deteriorated after one month. These cultures consisted of macrophage-like cells and could not be recovered by exposure to GM-CSF. The GM-CSF culture continued to respond with the pattern of culture expansion shown in FIG. 1, while maintaining an undifferentiated morphology described above for the uncultured cells. See: Bennett et al., supra.

The stringent growth requirement for GM-CSF was assayed by depriving the cells of GM-CSF and reseeding under varying culture conditions. The cultures assayed in generating the data for FIG. 1A were prepared from mononuclear cells constisting predominantly of leukemic blast cells obtained from a stock culture, seeded at $10^6$ cells/2 ml of nutrient medium (RPMI 1640 supplemented with 10% (v/v) heat-inactivated human serum) and grown for over four (4) months in GM-CSF. Cells were then washed and the pellet resuspended in the nutrient medium, which was supplemented with either IL-3 or GM-CSF (5 ng/ml). Other cultures were prepared using serum-free Iscove Modified Dulbecco Medium (IMDM) supplemented with insulin (10 ul/ml), transferrin (10 ug/ml), $10^{-4}$M mercaptoethanol, and either GM-CSF or IL-3 (5 ng/ml). Control cultures contained nutrient medium only. These cultures were maintained in 5% $CO_2$/95% air at 37° C. The unmodified nutrient medium was obtained from GIBCO, Grand Island, N.Y.; the growth factors were obtained from Amgen, Thousand Oaks, Calif. As can be seen in FIG. 1A, only cultures supplemented with GM-CSF survived. Neither nutrient medium nor IL-3-containing medium alone could support cell growth. FIG. 1B shows, in addition, that when cells were cultured in the serum-free medium, only GM-CSF was required for growth. These data indicate that long term proliferation of the cell line of the invention, by which is meant growth for over 12 months and 70 passages, is strictly dependent upon the continuous presence of GM-CSF.

The HU-01 cells can be subcultured continuously and indefinitely.

Once the cell line of the invention was over three (3) months in culture, extensive characterization was begun. Flow cytometric analysis of the cells, performed in the manner described by Janossy et al. in *Immunofluorescence and Immunochemistry*, pp. 67–83, G. Klaus, ed., IRL Press, (1987), showed a phenotype similar to fresh blood cells. Membrane markers were detected by monoclonal antibodies (MAB) and identified by cluster of differentiation (CD) nomenclature, as described by Hogg et al., in *Leucocyte Typing III*, pp. 576–602, A. McMichael, ed., Oxford Univ. Press (1987). The results of this assay are shown in Table I, below.

TABLE I

Surface Phenotype of GM-CSF Dependent Cells

| CD | MAB | Antigen Designation | Control[a] (% Positive) | TPA (% Positive) |
|---|---|---|---|---|
| 11b | CR3 | C3bi receptor | 66 | ND[b] |
|  | MO1 |  | 78 | 64 |
| 13 | MY7 | 150 KD | 77 | 73 |
| 21 | CR2 | C3d receptor | 66 | 0 |
| 33 | MY9 | 68 KD | 90 | 82 |
| 34 | HPCA | Stem cell | 72 | 56 |
|  | BI-3C5 |  | 92 | 82 |
| 35 | CR1 | C3b receptor | 86 | ND |
| 36 | 5F1 | GP IV | 94 | 91 |
|  | FA6 |  | 93 | 89 |
| 38 | Leu-17 | T10 | 92 | ND |
| W41 | 10E5 | GP IIb-IIIa | 7 | 69 |
| W42 | 6D1 | GP Ib | 0 | 0 |
| 45 | HLe-1 | Human leukocyte | 93 | 91 |
| — | H85 | Glycophorin A | 92 | 57 |
| — | TFR | Transferrin receptor | 92 | 64 |
| — | HLA | HLA-DR | 89 | 57 |

[a] Cells from a stock culture grown under standard GM-CSF conditions served as a control for cells exposed to $10^{-8}$M TPA for 48 hrs.
[b] ND = Not Done The predominant markers were found to be CD 34, the stem cell marker, and CD 13, 33, 36 and 38. Negative results were obtained in assays for CD 1a, 2–5, 7, 8, 10, 11c, 14, 15, 19, 20, 22, 25, as well as for B5, Leu-7 and Leu-19. The membrane markers determined for the cell line of the invention are consistent with a cell which may be the common precursor to red cells and platelets. See: Breton-Gorius et al., *Blood Cells*, 15:3 (1989); Greenberg et al., *Blood*, 72:1968 (1988); and Avanzi et al., supra. GPA was weakly expressed on over 90% of the cells as was the transferrin receptor. Expression of GP Ib and GP IIb-IIIa was lost after one month in culture. GP IIb-IIIa, but not GP-Ib, was subsequently inducible by a 24 hr exposure to phorbol esters, e.g., 12-o-tetradecanoylphorbol-13-acetate (TPA). The predominantly diploid cultured cells shared cytogenetic markers with the patient's bone marrow leukemia cells and were negative for Epstein-Barr virus and mycoplasma.

The histochemical profiles of fresh and cultured cells were identical. Both were negative for enzymes of the myeloid lineage, i.e., myeloperoxidase, chloroacetate esterase, alpha naphthol acetate esterase, but were positive for acid phosphatase and periodic acid Schiff (PAS). Cytogenetic analyses of thawed blood cells grown for six days and cells cultured for over 5 months in GM-CSF were similar to the abnormal karyotype of the bone marrow, which was already noted above.

These data characterizing the cell line indicate that GM-CSF is capable of sustaining a proliferating, non-differentiating hematopoietic progenitor cell derived from a leukemic clone.

The potential of the cell line of the invention to differentiate into megakaryocytes was indicated by the TPA induction of GP IIb-IIIa, but terminal maturation first occurred in the erythrocyte lineage.

Figure 2:
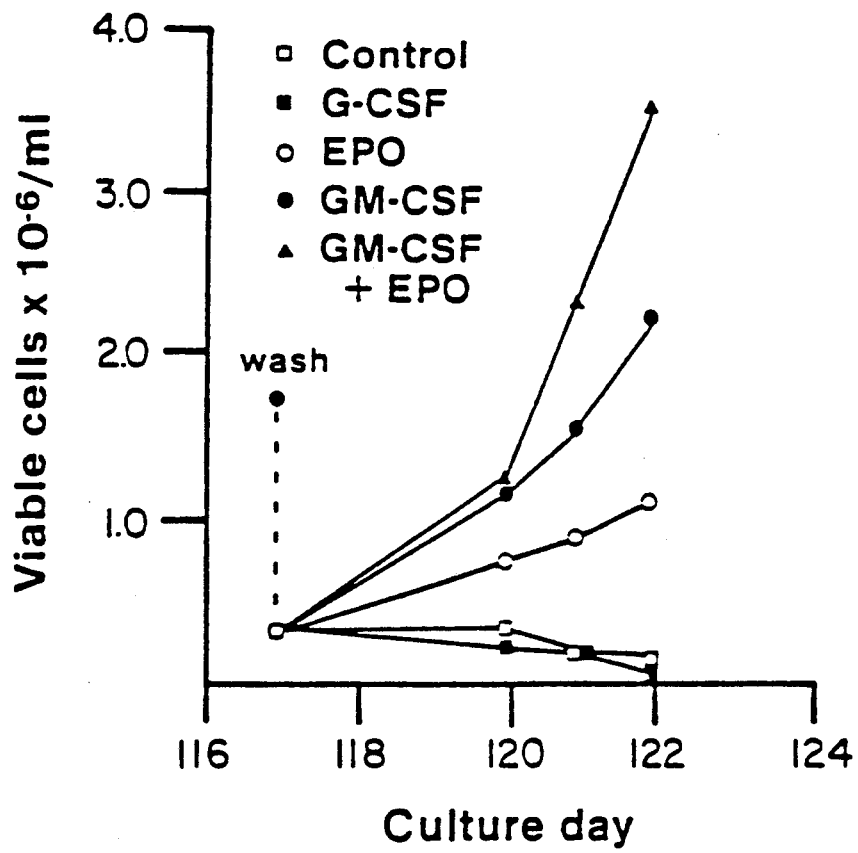
FIG. 2 is a graph representing the correlation between cell proliferation and length of time in culture for cultured HU-01 cells grown in the presence of various growth factors, individually and in combination, and illustrates the effects of erythropoietin (EPO) on the growth of the GM-CSF-dependent cell line of the invention.

Initially, optimal growth occurred when the serum source for the nutrient medium was an anemic donor which most likely contained a high titer of EPO. The influence of EPO on the cell line of the invention was apparent when growth of all GM-CSF cultures containing sera from various human donors was enhanced with the addition of EPO. Even cell growth in the culture supplemented with anemic serum was augmented with the addition of EPO. The effect of EPO-exposure on cell growth is shown in FIG. 2. The cells used to obtained the data reflected in FIG. 2 were four (4) months in culture. These cells were washed free of GM-CSF and recultured in nutrient medium supplemented with GM-CSF (5 ng/ml), EPO alone (4 units/ml) and in combination with GM-CSF (5 ng/ml). Cells were also recultured in nutrient medium supplemented with granulocyte-colony stimulating factor (G-CSF) (2.5 ng/ml). The control contained nutrient medium only.

Figure 3:
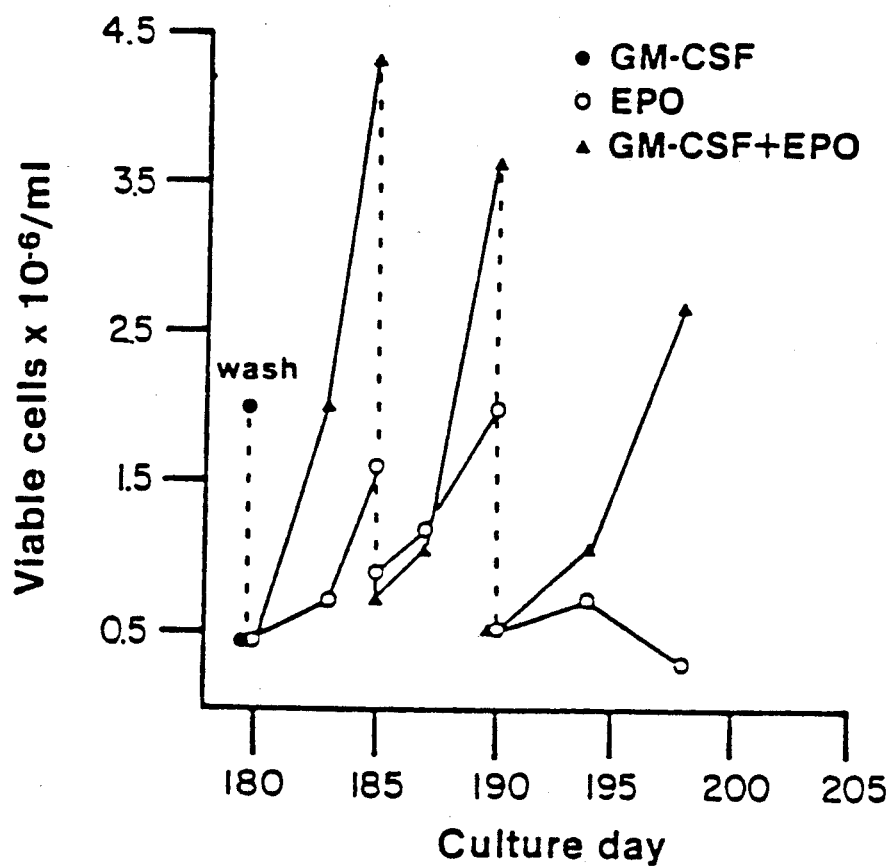
FIG. 3 is a graph representing the correlation between cell proliferation and length of time in culture for cultured HU-01 cells exposed to GM-CSF only, to EPO only and to GM-CSF and EPO in combination, and illustrates the short-term response of EPO-induced cells that are deprived of GM-CSF.

Exposure of the cells to EPO alone appeared to be able to support minimal cell growth, since cultures deprived of GM-CSF and replenished with EPO did not decline, as was the case for G-CSF and also for the GM-CSF-deprived control. This raised the possibility that EPO as well as GM-CSF could support cell growth. As shown in FIG. 3, however, when the GM-CSF-dependent cells, which had been in culture for six months, were washed and reseeded in nutrient medium containing EPO ( 4 units/ml) only, the observed effect of EPO was short-lived. Even though EPO supported sub-optimal growth for 10 days, cells were growth arrested and the cultures failed. These data not only confirmed the strict growth requirement for GM-CSF, but also indicated that EPO enhanced the previously observed factor-dependent growth and had a transient effect on cell growth in the absence of GM-CSF.

Figure 4A:
FIG. 4(A) and 4(B) depict microphotographs (magnification 1000 ×) of stained, EPO-induced HU-01 cells, showing the morphology of the GM-CSF dependent cells of the invention which are not induced with EPO (FIG. 4A), as compared with the distinct morphology of well-defined stages of erythocyte maturation (FIG. 4B).
Figure 4B:
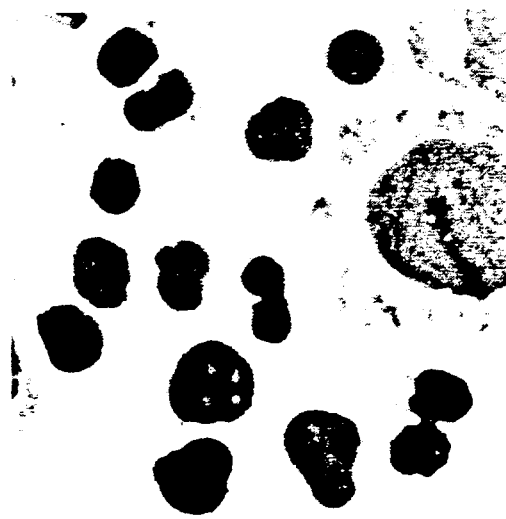

The most striking effect produced by EPO was not immediately evident. It was not until 7-10 days after exposure to EPO that a morphological change became apparent in the GM-CSF+EPO- containing culture and in the EPO-containing culture. As is apparent from FIG. 4, the morphology of the cells, which were deposited onto slides with a cytocentrifuge and stained with Wright-Giemsa differential blood stain, is distinctive for well-defined stages of erythrocyte maturation. Hemoglobin was detectable in these cells by benzidine staining in the manner described by D. Metcalf, in *Clonal Culture of Hemopoietic Cells*, p. 87, D. Metcalf ed., Elsevier (1984). Within 10 days after the addition of EPO, a relative and absolute increase in the hemoglobinized cells occurred and remained stable at 25-35% in the GM-CSF+EPO culture. When cells had been deprived of GM-CSF, proliferation ceased after 10 days growth in EPO followed by a four-fold increase in the number of benzidine positive cells and a relative frequency of 88% before the culture declined due to terminal differentiation.

The hemoglobin (Hb) types were subsequently identified by chain-specific monoclonal antibodies according to the procedure described by Morgan et al., *Journal of Cell Biology*, 100:565 (1985). Cells were washed free of GM-CSF and cultured with EPO. At varying times, cells were removed and deposited onto slides for detection of hemoglobin by benzidine staining and globin chain identification by indirect immunofluorescence. K562 was the positive control for the embryonic globin chains. The results of these assays are shown in Table II, below. As can be seen in Table II few uninduced cells contained fetal gamma chains (HbF) or adult beta chains (HbA). In a time-dependent response to EPO, an increase in the relative numbers of cells containing either HbF and/or HbA occurred. HbA was the predominant species prior to terminal differentiation. The embryonic zeta and epsilon chains were not detected.

TABLE II

| | EPO Induction of Hemoglobin | | | | |
|---|---|---|---|---|---|
| | Globin Chain (%) | | | | Benzidine Positive |
| Cell Line | gamma | beta | zeta | epsilon | (%) |
| HU-01 | | | | | |
| Uninduced | 2.2 | 1.5 | 0 | 0 | 2.0 |
| EPO Day 3 | 1.9 | 3.0 | 0 | 0 | 6.0 |
| 5 | 4.9 | 6.2 | 0 | 0 | 8.4 |
| 7 | 14.6 | 12.0 | 0 | 0 | 20.8 |
| 13 | 23.3 | 63.3 | 0 | 0 | 44.9 |
| Control | 0 | 0 | 22.7 | 2.7 | 0 |

The indirect immunofluorescence procedure referred to above was employed in determining the expression of selected antigenic markers after EPO-induction of the cell line of the invention. The stock GM-CSF culture was washed 35 days prior to the testing and continued in GM-CSF, with and without EPO. After 25 days, part of the GM-CSF+EPO culture was washed and continued for 10 days in EPO alone until terminal differentiation occurred. The results of this assay are set forth in Table III, below.

TABLE III

Modulation of Membrane Antigens by EPO-induced Differentiation of GM-CSF Dependent Cells.

| Growth Factor | Post-EPO (Days) | GM-Free (Days) | MY7 | MY9 | MY10 | 5F1 | GPA | CA | Fetal Hb | Benzidine |
|---|---|---|---|---|---|---|---|---|---|---|
| | | | | | (Percent Positive Cells) | | | | | |
| GM-CSF | 0 | 0 | 30 | 51 | 78 | 92 | 64 | 26 | 9 | 1 |
| GM-CSF + EPO | 35 | 0 | 11 | 25 | 16 | 94 | 87 | 44 | 28 | 22 |
| EPO | 35 | 10 | 0 | 3 | 5 | ND[a] | ND | ND | 20 | 80 |

[a]ND = Not Done

During the maturation of the primitive cultured cells of the invention, the modulation of certain markers was observed. Markers previously described for granulocytes, namely MY7 and MY9, were lost, as was the stem cell marker MY10. Meanwhile, the erythrocyte-associated CA, GPA and fetal Hb markers were enhanced.

These observations and the test data set out in Table III indicate that the markers found on primitive cells are retained by the granulocytes and are lost by non-granulocytes during maturation.

The cell line of the invention is inhibited by transforming growth factor-beta (TGF-b). The inhibiting effect of TGF-b was determined by cell growth assays. Stock cultures deprived of GM-CSF were cultured in nutrient medium containing either GM-CSF (5 ng/ml) or EPO (4 units/ml). TGF-b1 and TGF-b2 were added separately, in varying amounts, to each of the cultures. TGF-b1 (1 ng/ml) was the more effective inhibitor of cell growth and arrested both the GM-CSF and the EPO-induced growth responses. TGF-b2 (5 ng/ml) retarded, but did not arrest the GM-CSF-induced growth. At lower concentration (1 ng/ml), TGF-b2 arrested the EPO-induced growth response. EPO-induced erythrocyte maturation, however, progressed in the cultures containing either species of TGF-b at the amounts used. Hemoglobin-containing cells accumulated in all EPO-induced cultures, but these cultures declined more quickly in those exposed to TGF-b.

The cell line of the invention may be used for production of monoclonal antibodies against human leukemia cells. Monoclonal antibody production can be carried out using conventional techniques, by immunizing a suitable murine host with HU-01 cells, fusing spleen cells from the host with myeloma cells to provide an immortal hybrid cell line, selecting antibody-producing hybrid cells, determining binding selectively with various cell types and culturing those cells producing HU-01-specific antibodies in vitro, or transplanting them into mice with subsequent production of ascites fluid. The production of such antibodies would enable the identification and characterization of leukemic cells at an early stage of development when they are difficult to classify, thereby allowing early diagnosis and determination of an appropriate therapeutic protocol. The monoclonal antibodies may themselves by coupled with an appropriate cytotoxic agent for leukemia therapy.

It is anticipated that the factor(s) which mediates globin gene expression may be derivable from HB-01 cells using established recombinant DNA techniques. Thus, it is quite possible that the gene(s) responsible for regulation of the globin gene switch can be isolated, cloned, and expressed in a suitable host system to enable large scale production of the gene product, such product having potential utility in augmenting fetal hemoglobin production, which will be of substantial clinical benefit to patients with severe thalassemia and sickle-cell anemia. *Molecular Basis of Blood Diseases*, supra, at 95. Other regulatory factors associated with activation of erythroid-specific genes may be similarly derived from the HB-01 cell line.

The human cell line described hereinabove has additional utility in that it provides an in vitro system which should substantially advance understanding of the molecular and cell biology of cell growth and differentiation. As described above, the cell line of the invention produces fetal and then adult hemoglobin during the course of ertyrocyte maturation. This switch in the globin genes will provide a model system for studying the control of gene expression during cell differentiation.

The cell line of the invention, HU-01, having the above-described properties and characteristics, was deposited at the American Type Culture Collection (ATCC), Rockville, Md. on Oct. 3, 1989 and was assigned Accession No. CRL 10249.

Although the present invention has been described in terms of a preferred embodiment, other embodiments may be apparent to those skilled in the art. The invention is, therefore, not limited to the particular embodiment described, but may be capable of modification or variation without departing from the spirit of the invention, the full scope of which is delineated by the appended claims.

What is claimed is:

1. A cultured, GM-CSF dependent, hematopoietic human cell line, HU-01 having ATCC accession number CRL 10249, which exhibits EPO-induced terminal erythrocyte maturation.

2. A cell culture comprising cells of the cell line of claim 1 in a nutrient culture medium including GM-CSF.

3. A cell culture according to claim 2 comprising said cells suspended in RPMI 1640 containing 10% (v/v) human serum, as the nutrient culture medium.

* * * * *